United States Patent
Kasuya

(10) Patent No.: US 7,796,736 B2
(45) Date of Patent: Sep. 14, 2010

(54) X-RAY CT APPARATUS AND A METHOD OF CONTROLLING THE SAME

(75) Inventor: Yuichi Kasuya, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 49 days.

(21) Appl. No.: 12/193,283

(22) Filed: Aug. 18, 2008

(65) Prior Publication Data
US 2009/0060122 A1    Mar. 5, 2009

(30) Foreign Application Priority Data
Aug. 31, 2007    (JP)    ............... 2007-225213

(51) Int. Cl.
*H05G 1/24*    (2006.01)
(52) U.S. Cl. .......................................... 378/103; 378/4
(58) Field of Classification Search .................. 378/4, 378/103
See application file for complete search history.

(56) References Cited

U.S. PATENT DOCUMENTS 5,761,269 A    6/1998    Sugihara et al.
2006/0187691 A1*    8/2006    Beland ..................... 363/71
2006/0210013 A1*    9/2006    Kasuya ....................... 378/4
2008/0112537 A1*    5/2008    Katcha et al. ............ 378/102

FOREIGN PATENT DOCUMENTS

| JP | 9-56710 | 3/1997 |
| JP | 9-276262 | 10/1997 |
| JP | 2002-336236 | 11/2002 |
| JP | 2006-289066 | 10/2006 |

* cited by examiner

*Primary Examiner*—Chih-Cheng G Kao
(74) *Attorney, Agent, or Firm*—Oblon, Spivak, McClelland, Maier & Neustadt, L.L.P.

(57) ABSTRACT

An X-ray-generator irradiates X-rays at a subject. The X-ray-detector detects the X-rays that have permeated the subject. The rotating body on which the X-ray-generator and the X-ray-detector are installed rotates around the subject. The rotating body is rotated by the drive part. The power source supplies electrical power to the drive part. The step-down part lowers the voltage of the regenerative electrical power generated at the drive part during the deceleration of the rotating body. The accumulation part charges the lowered electrical power. The step-up part raises the voltage of the electrical power from the accumulation part and supplies electrical power to the drive part.

12 Claims, 7 Drawing Sheets

X-RAY CT APPARATUS AND A METHOD OF CONTROLLING THE SAME

BACKGROUND OF THE INVENTION

1. Field of the Invention

The present invention relates to an X-ray CT apparatus that reuses regenerative energy and a method of controlling the same.

2. Description of the Related Art

In the field of an X-ray computer tomography apparatus (an X-ray CT apparatus) that performs tomography of a subject by using X-rays, efforts have been made on a daily basis in various aspects such as the facilitation of multifunctionality, sophisticated performance, and the shortening of imaging time. However, the amount of heat that is released tends to increase as the performance and functionality of these apparatuses improves.

As such technological innovation advances, the issue of how to externally release the heat that is generated as a byproduct inside the apparatus has been studied in conjunction.

A representative of the heat generated inside the X-ray CT apparatus is attributable to the regenerative resistance. Regenerative resistance is a resistance element that is provided to convert into heat energy electromotive force energy generated during the deceleration of the rotation of a motor for driving a rotating body that performs tomography of a subject while rotating (e.g., direct drive motor or the like). Therefore, when the motor frequently accelerates/decelerates, such as when consecutively imaging multiple subjects or when a service engineer performs maintenance or the like, the regenerative resistance may reach a considerable temperature. As a constitution for addressing such a situation, the technology of simply increasing the quantity of regenerative resistance, and furthermore, for example, the following technologies have heretofore been known.

Some X-ray CT apparatuses are installed so that heat tends to be released outside the apparatus by providing regenerative resistance on the upper portion of a mounting base, and often adopts a constitution that brings the regenerative resistance is contact with a metal portion within the mounting base to enable the heat to escape from the metal portion.

Meanwhile, for an X-ray CT apparatus in which it is difficult to ensure a sufficient space for installing the regenerative resistance on the upper portion of a mounting base, the lateral portion of the apparatus is often provided with the regenerative resistance.

Among the X-ray CT apparatuses as described above, those having an additional constitution such as a fan for externally guiding the heat generated by the regenerative resistance has also heretofore been known. For example, Japanese Unexamined Patent Application No. H9-276262 discloses an X-ray CT apparatus that is provided with a suction opening on the upper portion of the imaging opening and with a cooling fan on the upper portion of the apparatus respectively and releases the heat by generating airflow inside the apparatus.

In addition, an X-ray CT apparatus has been proposed that is configured to release the heat inside the apparatus by rotating a plurality of blade members along with a rotating part of a mounting base to convey air to a supporting member (X-ray computer tomography apparatus, e.g., Japanese Unexamined Patent Application No. H9-56710).

Similar to the constitution described in Japanese Unexamined Patent Application No. H9-276262, this also attempts to release the heat by keeping favorable ventilation inside the apparatus.

Moreover, an X-ray CT scan system has been disclosed comprising a regenerative resistance apparatus provided inside the mounting base (X-ray CT apparatus) and a blower fan for transferring the heat generated by this regenerative resistance apparatus to a top plate of a carrying apparatus on which to place a subject (e.g., Japanese Unexamined Patent Application Publication No. 2002-336236). This X-ray CT scan system makes it possible to achieve a heating action for a subject by warming the top plate. It also adopts the method of cooling the regenerative resistance by using airflow.

In addition, technology has also been proposed of accumulating the regenerative energy in a condenser without change to reuse the same (e.g., Japanese Unexamined Patent Application Publication No. 2006-289066).

Herein, by way of example, a conventional X-ray CT apparatus with a constitution in which heat is released by a regenerative resistance will be described below with reference to FIG. 1 and FIG. 2.

FIG. 1 is a front perspective diagram showing an outline of the constitution of a conventional X-ray CT apparatus. In addition, FIG. 2 is a block diagram showing the constitution of a conventional X-ray CT apparatus. As shown in FIG. 1, an X-ray CT apparatus 1 is an apparatus for irradiating X-rays while scanning a subject and for detecting the X-rays that have permeated the subject. This X-ray CT apparatus 1 constitutes an X-ray tomographic imaging system along with a bed for carrying a subject placed on a top plate to the imaging position (imaging opening described above), a computer for analyzing the detected data of the X-ray CT apparatus 1 to reconstruct and display the X-ray tomographic image (neither are shown) or the like and uses the same.

An opening provided near the center of a package 2 of the X-ray CT apparatus 1 forms an imaging opening 3 into which the subject placed on the top plate described above is to be inserted. The package 2 houses a wide variety of instruments for irradiating X-rays at a subject from various directions and detecting the X-rays that have passed through the subject, including a motor 4 such as a direct drive motor, a rotating body 5, an inverter part 6, and the like. In addition, a regenerative resistance 7 is connected to the inverter part 6.

The rotating body 5 is a frame body that is arranged so as to surround the imaging opening 3 and is rotated by the motor 4. On the rotating body 5 (supporting unit), an X-ray tube 8 (X-ray-generating unit) for outputting X-rays and a detector 9 (detecting unit) for detecting the X-rays outputted from this X-ray tube 8 are supported in an opposing arrangement. In addition, an AC/DC converter 10 for supplying a power source to the X-ray tube 8 and the detector 9, a signal-processing apparatus 11 for processing the results of detection by the detector 9, and the like, are attached to the rotating body 5.

The inverter part 6 comprises IGBTs (Insulated Gate Bipolar Transistors) 12 or the like. The inverter part 6 adjusts the voltage and frequency of the power source to be supplied to the motor 4 based on signals sent from the control part (control unit) and controls the drive, stopping, rotational speed, and the like of the motor 4. Incidentally, the motor 4 and the inverter part 6 constitute a drive unit in the present invention.

The regenerative resistance 7 is a member for converting the electrical energy (regenerative energy) that is generated during the deceleration of the motor 4 and flows backward into the inverter part 6 to be converted into heat energy for consumption of the same.

Incidentally, a regenerative resistance is also provided within the inverter part 6, while the regenerative resistance 7 is used in consuming regenerative energy that cannot be processed by this embedded regenerative resistance. Herein, the regenerative resistance 7 is installed, for example, on the upper portion of the side surface of the package 2 of the X-ray CT apparatus 1, as is conventionally done, and is structured so as to be thermally connected to a heat-releasing member or the like for releasing heat externally.

Each member installed in such a manner is configured as shown in FIG. 2. As shown in FIG. 2, the AC/DC converter 10 is connected to the motor 4 via the inverter part 6 consisting of switching elements such as IGBTs. The regenerative resistance 7 is interposed into the transmission path between the AC/DC converter 10 and the IGBTs and, during the deceleration of the motor 4, conveys the generated regenerative energy to the regenerative resistance 7 connected to the heat-releasing member for conversion of the same into heat.

In an X-ray CT apparatus with such a constitution, firstly, the imaging processing by an X-ray tomographic imaging system including the X-ray CT apparatus 1 is executed, in the process as follows. In FIG. 2, the switch SW1 is initially connected to the AC/DC converter 10.

The X-ray CT apparatus 1 supplies power from the inverter part 6 to the motor 4 to rotate the rotating body 5, irradiates X-rays from the X-ray tube 8, and detects the X-rays that have permeated the subject who is moved into the imaging opening 3 by the detector 9.

Then, the X-ray tube 8 and the detector 9 operate by receiving power from the AC/DC converter 10. The permeated X-rays that have been detected by the detector 9 are processed by the signal-processing apparatus 11 and converted into image data, and are then sent to the computer described above. Then, this computer reconstructs the image data into an image and displays a tomographic image of the subject.

After the imaging processing described above has been repeatedly executed, the energy based on the return electromotive force during the deceleration of the motor 4 (detected by the control part 100 itself), that is regenerative energy, is generated in a large amount. This regenerative energy is sent to the regenerative resistance 7 by the control part 100 turning on the switch SW1 into the side of the regenerative resistance 7, and the heat is released by a heat-releasing member thermally connected to the regenerative resistance 7.

However, the development of X-ray CT is currently moving in the direction of reducing the burden on a subject by shortening the imaging time. Thus, in order to shorten the imaging time, it is necessary to shorten the scanning time. In other words, it is necessary to rotate the rotating body at a higher speed, that is, to control the motor at high-speed rotation. In this regard, however, because the motor must be rapidly accelerated/decelerated in order to achieve this objective, a larger amount of regenerative energy is generated than in the past, so technology for effectively releasing heat or efficiently reusing the generated large amount of regenerative energy is required.

In other words, a so-called air-cooled heat releasing function described in Patent Documents 1 through 3 requires a large-capacity regenerative resistance for the release of heat energy increased by the accelerated rotation of the rotating body, thereby making it difficult to achieve a simplification of the constitution and a reduction in the manufacturing cost.

In addition, for the technology described in Patent Document 4, it is difficult to make the X-ray CT apparatus more compact, because regenerative energy is accumulated without change and the capacity of the accumulating portion thus becomes larger.

SUMMARY OF THE INVENTION

The purpose of the present invention is to provide an X-ray CT apparatus that is capable of making effective use of the regenerative energy that has accumulated in the regenerative resistance with a simple and compact constitution as well as a method of controlling the same.

The X-ray CT apparatus in the first mode of the present invention comprises the following functioning parts. The X-ray-generator irradiates X-rays at a subject. The X-ray-detector detects the X-rays that have permeated said subject. The rotating body on which said X-ray-generator and said X-ray-detector are installed rotates around said subject. Said rotating body is rotated by the drive part. The power source supplies electrical power to said drive part. The step-down part lowers the voltage of the regenerative electrical power generated at said drive part during deceleration of said rotating body.

The accumulation part charges said lowered electrical power.

The step-up part raises the voltage of the electrical power from said accumulation part and supplies electrical power to said drive part.

The X-ray CT apparatus in the second mode of the present invention comprises the following functioning parts. The bed is a base on which to place a subject. The bed drive part drives said bed. The X-ray-generator irradiates X-rays at a subject. The X-ray-detector detects the X-rays that have permeated said subject. The rotating body on which said X-ray-generator and said X-ray-detector are installed rotates around said subject. Said rotating body is rotated by the drive part. The step-up part raises the alternating-current voltage that is entered externally. The AC/DC conversion part converts said raised alternating-current voltage into direct-current voltage to convey the same to said drive part during rotating said rotating body, and when said rotating body decelerates, converts the regenerative electrical power generated at said drive part during the deceleration of said rotating body into an alternating-current voltage to supply electrical power to at least one of said bed drive part or image-processing part.

The method of controlling the X-ray CT apparatus in the third mode of the present invention comprises the following stages: a stage of electrical power being supplied by a power source; a stage of switching the power supply pathway to the pathway coming from said power source; a stage of rotary driving of a rotating body around a subject via a drive part by using said supplied electrical power; an X-ray-generating stage for irradiating X-rays at said subject from the X-ray-generator installed on said rotating body; an X-ray-detecting stage for detecting the X-rays that have permeated said subject via the X-ray-detector installed on said rotating body; a step-down stage for lowering the voltage of regenerative electrical power generated at said drive part during deceleration of said rotating body; an accumulation stage for charging said lowered electrical power into said accumulation part; and a stage of raising the voltage of electrical power from said accumulation part by a step-up part and supplying electrical power to said drive part in order to drive said rotating body.

The method of controlling the X-ray CT apparatus in the fourth mode of the present invention comprises the following stages: a pressure-raising stage for raising the alternating-current voltage that is entered externally; a stage of converting said raised alternating-current voltage into direct-current voltage to convey the same to a drive part for the rotary driving of a rotating body; a stage of rotary driving of said rotating body around a subject via said drive part; an X-ray-generating stage for irradiating X-rays at said subject from the X-ray-generator installed on said rotating body; an X-ray-detecting stage for detecting the X-rays that have permeated said subject via the X-ray-detector installed on said rotating body; a stage of converting the regenerative electrical power generated at said drive part during deceleration of said rotating body into an alternating-current voltage; and a stage of supplying said alternating-current voltage to at least one of a bed drive part for driving a bed or an image-processing part.

According to the first and third modes, it becomes possible to lower the voltage of and accumulate regenerative energy. This eliminates the need for releasing heat and thus the need to install a large regenerative resistance, so the capacity of the accumulation part can be made smaller. Therefore, it is possible to simplify the constitution of the X-ray CT apparatus and to make the apparatus more compact. In addition, because the accumulated regenerative energy is used for driving the rotating body, the reuse of energy can contribute to energy saving.

According to the second and fourth modes of the present invention, it becomes possible to use regenerative energy without change for other mechanisms in the X-ray CT apparatus, such as a bed drive part or a console. This eliminates the need for accumulating the regenerative energy, thereby making it possible to be more compact. In addition, because the regenerative energy is used for other mechanisms, the reuse of energy can contribute to energy saving.

DETAILED DESCRIPTION OF THE EMBODIMENTS

Embodiment 1

Figure 3:
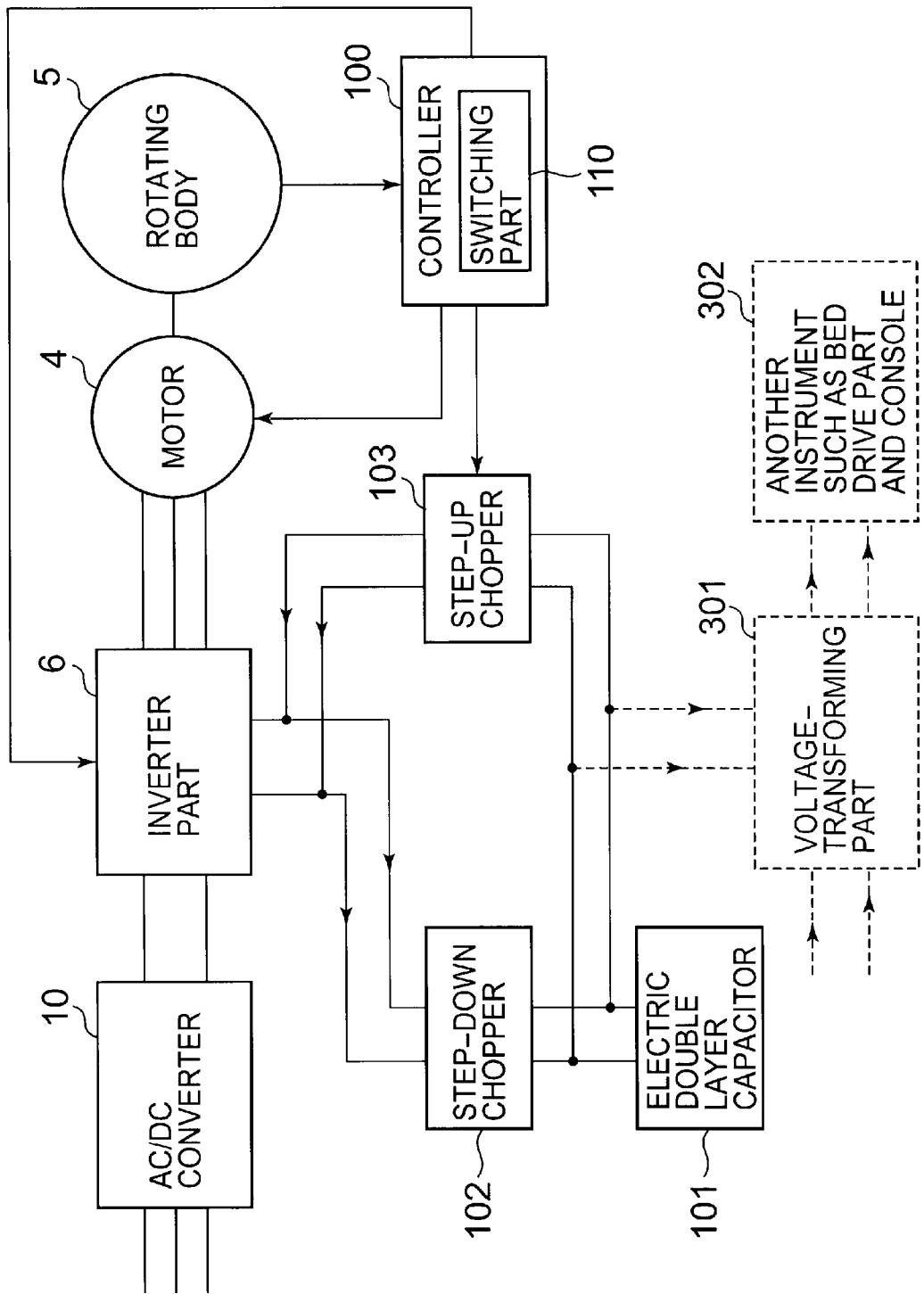
FIG. 3 is a block diagram of an X-ray CT apparatus according to the present invention.

Hereinafter, an X-ray CT apparatus according to the first embodiment of the present invention will be described. FIG. 3 is a block diagram representing the functions of the X-ray CT apparatus according to the present embodiment. The operator performs the setting of the X-ray irradiation and the like by using a console (not shown) or the like.

The AC/DC converter 10 is connected to the motor 4 via the inverter part 6. The AC/DC converter 10 converts the electrical power of a three-phase AC voltage from a commercial power source (alternating-current voltage) into DC voltage (direct-current voltage) electrical power and conveys the same to the inverter part 6. Herein, the AC/DC converter 10 is equivalent to the "power source" in the present invention.

The inverter part 6 comprises switching elements such as IGBTs.

During rotary driving of the rotating body 5, the switching elements are controlled so as to supply electrical power from the side of the AC/DC converter 10 based on a control signal from the switching part 110. Thus, the inverter part 6 converts the DC voltage received from the AC/DC converter 10 into a pulse voltage and conveys the same to the motor 4.

In addition, during deceleration of the rotating body 5, in response to an instruction from the control part 100, the switching elements are controlled so as to supply electrical power to the side of the Electric Double Layer Capacitor 101 based on the control signal from the switching part 110, and the inverter part 6 conveys the regenerative electrical power conveyed from the motor 4 to the step-down chopper 102. Then, the voltage conveyed from the inverter part 6 to the motor 4 is a high voltage, amounting to a few hundred volts.

Moreover, after completion of the charge into the Electric Double Layer Capacitor 101, when rotating the rotating body 5 in response to an instruction from the control part 100, the inverter part 6 conveys the electrical power conveyed from the step-up chopper 103 to the motor 4.

For rotary driving of the rotating body 5, the motor 4 drives the rotating body 5 by using the electrical power of the pulse voltage received from the inverter part 6. In addition, during deceleration of the rotating body 5, the motor 4 generates DC voltage regenerative electrical power. The motor 4 conveys the generated DV voltage to the inverter part 6.

Herein, the inverter part 6 and motor 4 is included in the "drive part" in the present invention.

Due to rotary driving of the rotating body 5, the X-ray-generator (not shown) and the X-ray-detector (not shown) that are attached to the rotating body 5 rotate around a subject. In this rotated state, X-rays are irradiated at a subject placed on a bed from the X-ray-generator. Furthermore, the X-ray-detector detects the X-rays that have passed through the subject. In addition, the bed is driven by the bed drive part. After imaging via the X-ray irradiation, the rotating body 5 starts to decelerate.

The step-down chopper 102 receives the regenerative electrical power conveyed from the inverter part 6 and lowers the voltage of the electrical power. For this stepping down, for example, the step-down chopper 102 lowers the voltage of the electrical power by converting the DC voltage received from the inverter part 6 into a pulse waveform, then lowering the voltage by using a transformer or the like, and then returning the same to a DC voltage again. The electrical power that has been lowered via the step-down chopper 102 is charged into the Electric Double Layer Capacitor 101. The step-down chopper 102 is equivalent to the "step-down part" in the present invention. Herein, in the present embodiment, it is desirable to use the voltage prior to step-down. Alternatively, it is desirable to adapt the degree of stepping down, which is to keep the withstand voltage of the Electric Double Layer Capacitor 101 low, to the voltage prior to stepping down or the capacity of the Electric Double Layer Capacitor 101 in order to calculate the voltage after the step-down.

The Electric Double Layer Capacitor 101 comprises a condenser, particularly a capacitor, and the voltage is charged by much of the capacity thereof. Then, the capacity of the Electric Double Layer Capacitor 101 is configured to have a sufficient capacity for the capacity calculated based on the rotational speed of the rotating body, the voltage to be used, the rate of voltage to be lowered, and the like.

Thus, the Electric Double Layer Capacitor 101 can be charged without being saturated with regenerative electrical power. In addition, the voltage of electrical power to be charged has been lowered by stepping down, so the withstand voltage of the Electric Double Layer Capacitor 101 may be small. The Electric Double Layer Capacitor 101 has a faster charging speed and discharging speed than those of a simple condenser. This makes it possible to charge all of the conveyed electrical power and to sufficiently discharge it for the required electrical power. The Electric Double Layer Capacitor 101 is equivalent to the "accumulation part" in the present invention.

The control part 100 comprises a storage part such as a CPU and memory, and further has a switching part 110. A prescribed value of the voltage that is the basis of switching of the power supply pathways in the Electric Double Layer Capacitor 101 (hereinafter referred to as "minimum voltage") is stored in the storage part of the control part 100 in advance. Upon receipt of entry of the start of an X-ray imaging (X-ray CT scan) from a console (not shown) or the like, the control part 100 sends an instruction to start rotation of the rotating body 5 to the inverter part 6 and the motor 4. Then, the control part 100 continuously obtains the rotational speed of the rotating body 5 from the detector.

When the control part 100 has received an entry to start X-ray imaging, the switching part 110 switches the operation of the switching elements so as to switch the pathway of the power supply to the inverter 6 and the motor 4 to a pathway on the side of the commercial power source, that is, a pathway for receiving power from the AC/DC conversion part 10 when the voltage of the Electric Double Layer Capacitor 101 is less than the minimum voltage. In addition, when the voltage of the Electric Double Layer Capacitor 101 is greater than the minimum voltage, the switching part 110 switches the operation of the switching elements so as to switch the pathway of the power supply to the inverter 6 and the motor 4 to a pathway for receiving power from the Electric Double Layer Capacitor. Herein, the control part 100 is equivalent to the "control part" in the present invention. In addition, the switching part 110 is equivalent to the "switch control part" in the present invention.

Next, at the timing of the end of the X-ray diagnosis that has been preset by the console or the like, the control part 100 sends an instruction for stopping the rotating body 5 to the inverter part 6 and the motor 4. When the number of rotations of the rotating body 5 is 0, that is, when the rotating body 5 stops, the control part 100 connects the step-up chopper 103 to the power supply line. Furthermore, when the voltage of the Electric Double Layer Capacitor 101 is less than the minimum voltage, the switching part 110 disconnects the step-up chopper 103 from the power supply line and switches the switching elements to the power supply pathway on the side of the commercial power source, that is, on the side of the AC/DC converter 10.

The step-up chopper 103 raises the voltage conveyed from the Electric Double Layer Capacitor 101. For this stepping-up, for example, the step-up chopper 103 converts the DC voltage received from the Electric Double Layer Capacitor 101 to an alternating-current voltage such as a pulse waveform, then raises the voltage using a transformer or the like, and returns the same to a DC voltage again. Furthermore, the step-up chopper 103 conveys the raised voltage to the inverter part 6. The step-up chopper 103 is equivalent to the "step-up part" in the present invention.

Figure 4:
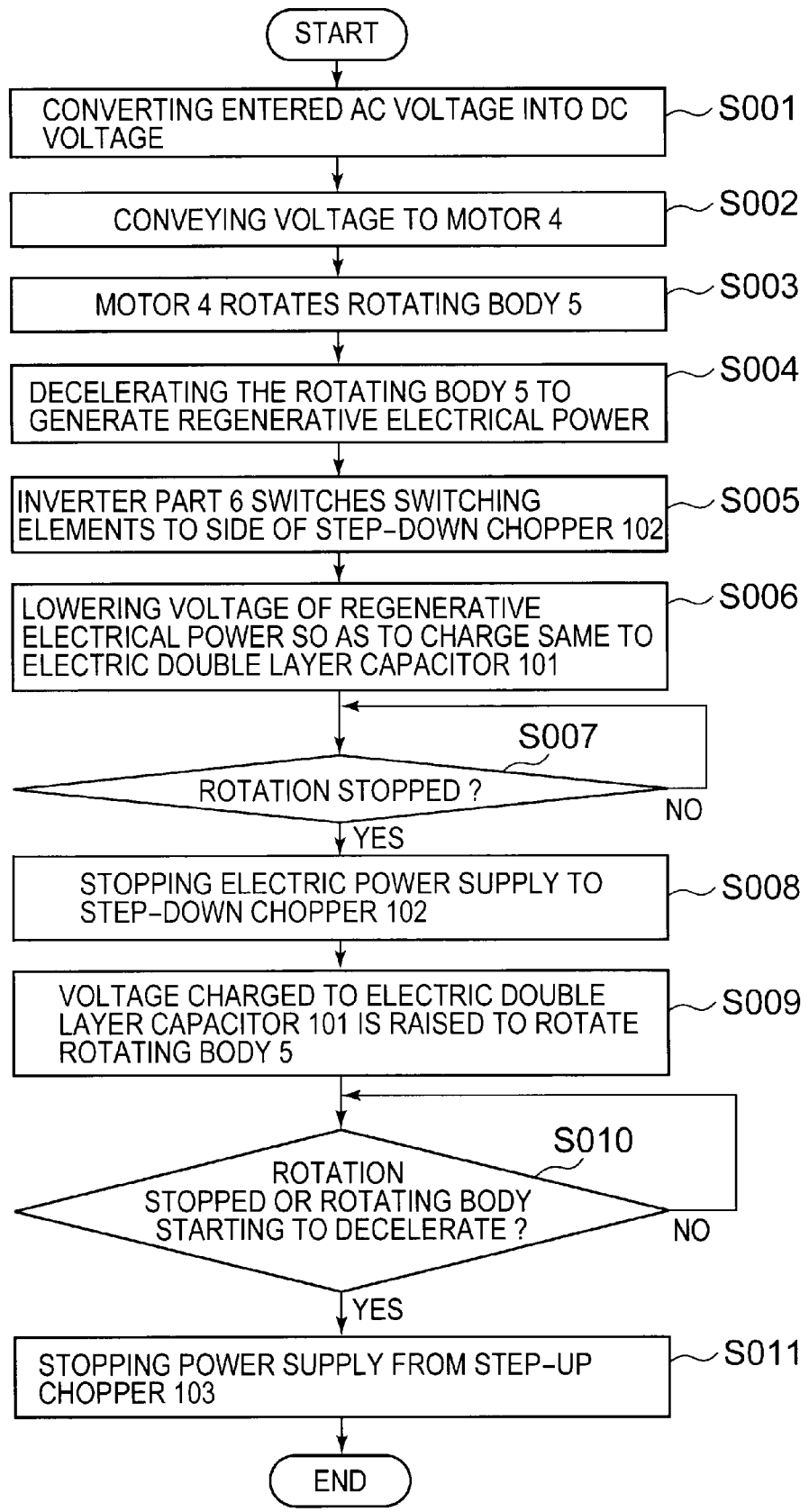
FIG. 4 is a flow chart of the charge and release of regenerative electrical power in the X-ray CT apparatus according to the present invention.

Next, the operations of charge and release in the X-ray CT apparatus according to the present embodiment will be described with reference to FIG. 4. FIG. 4 is a flow chart of charge and release in the X-ray CT apparatus according to the present embodiment.

Step S001: The AC/DC converter 10 converts the entered AC voltage into a DC voltage.

Step S002: Upon receiving an instruction from the switching part 110 included in the control part 100, the inverter part 6 switches the operation of the switching elements so as to form a power supply route to the side of the motor 4, converts the DC voltage conveyed from the AC/DC converter 10 to an AC voltage, for example, by controlling PWM (Pulse Width Modulation), and conveys the same to the motor 4.

Step S003: The motor 4 rotates the rotating body 5 by using the AC voltage conveyed from the inverter part 6.

Step S004: The control part 100 sends an instruction for stopping the rotating body 5 to the inverter part 6 and the motor 4 when it is determined that it has reached the prescribed timing (when the X-ray imaging is complete). This decelerates the rotating body 5. A regenerative electrical power is generated at the motor 4 due to the deceleration.

Step S005: The switching part 110 switches the operation of the switching elements so as to form a power supply route to the side of the step-down chopper 102, and the inverter part 6 conveys the regenerative electrical power conveyed from the motor 4 to the step-down chopper 102.

Step S006: The step-down chopper 102 lowers the voltage of the electrical power conveyed from the inverter part 6 so as to supply the same to the Electric Double Layer Capacitor, and the Electric Double Layer Capacitor 101 charges the electrical power.

Step S007: When the rotational speed of the rotating body 5 is 0, that is, when the rotating body 5 stops, or when the rotational speed is less than the prescribed rotational speed, the control part 100 proceeds to Step S008.

Step S008: The control part 100 switches the operation of the switching elements of the inverter part 6 so as to disconnect the power supply pathway from the motor 4 to the step-down chopper 102 and to stop the power supply. In addition, at the same time, the control part 100 switches the operation of the switching elements of the step-up chopper 103 and the inverter part 6 so as to supply the electrical power that is charged in the Electric Double Layer Capacitor 101 to the inverter part 6 via the step-up chopper 103 in order to drive the motor 4.

Step S009: After stopping the rotation, when given an instruction to rotate the rotating body 5, the switching elements in the inverter part 6 are driven so as to form a power supply pathway to the side of the step-down chopper 102 in order to supply the electrical power of the direct-current voltage that has been raised by the step-up chopper 103 to the motor 4. Electrical powers are supplied via the power supply pathway from the step-up chopper 103 to the motor 4, during which the electrical power of the DC voltage is converted into the electrical power of an AC voltage for driving the motor. The motor 4 rotates the rotating body 5 by using the conveyed electrical power.

Step S010: The control part 100 determines whether it has changed to either a state in which the voltage of the Electric Double Layer Capacitor 101 is less than the prescribed value stored in advance or in which deceleration of the rotating body 5 has started (the rotating body 5 begins to decelerate when the next acceleration has started).

When the voltage of the Electric Double Layer Capacitor 101 is less than the prescribed value or when deceleration of the rotating body 5 has started, it proceeds to Step S011.

Step S011: The switching part 110 included in the control part 100 switches the operation of the switching elements so as to stop the power supply from the step-up chopper 103 and to receive the power supplied from the side of the commercial power source.

As described above, the X-ray CT apparatus according to the present embodiment lowers the voltage of the regenerative electrical power generated by deceleration of the rotating body and then charges the same to the Electric Double Layer Capacitor. This makes it possible to keep the withstand voltage of the Electric Double Layer Capacitor low. In addition, because the Electric Double Layer Capacitor is used as a condenser for charging, it is possible to shorten the charge time and the discharge time. Furthermore, it is also possible to save energy by reusing the charged electrical power for rotary driving of the rotating body.

Embodiment 2

Figure 5:
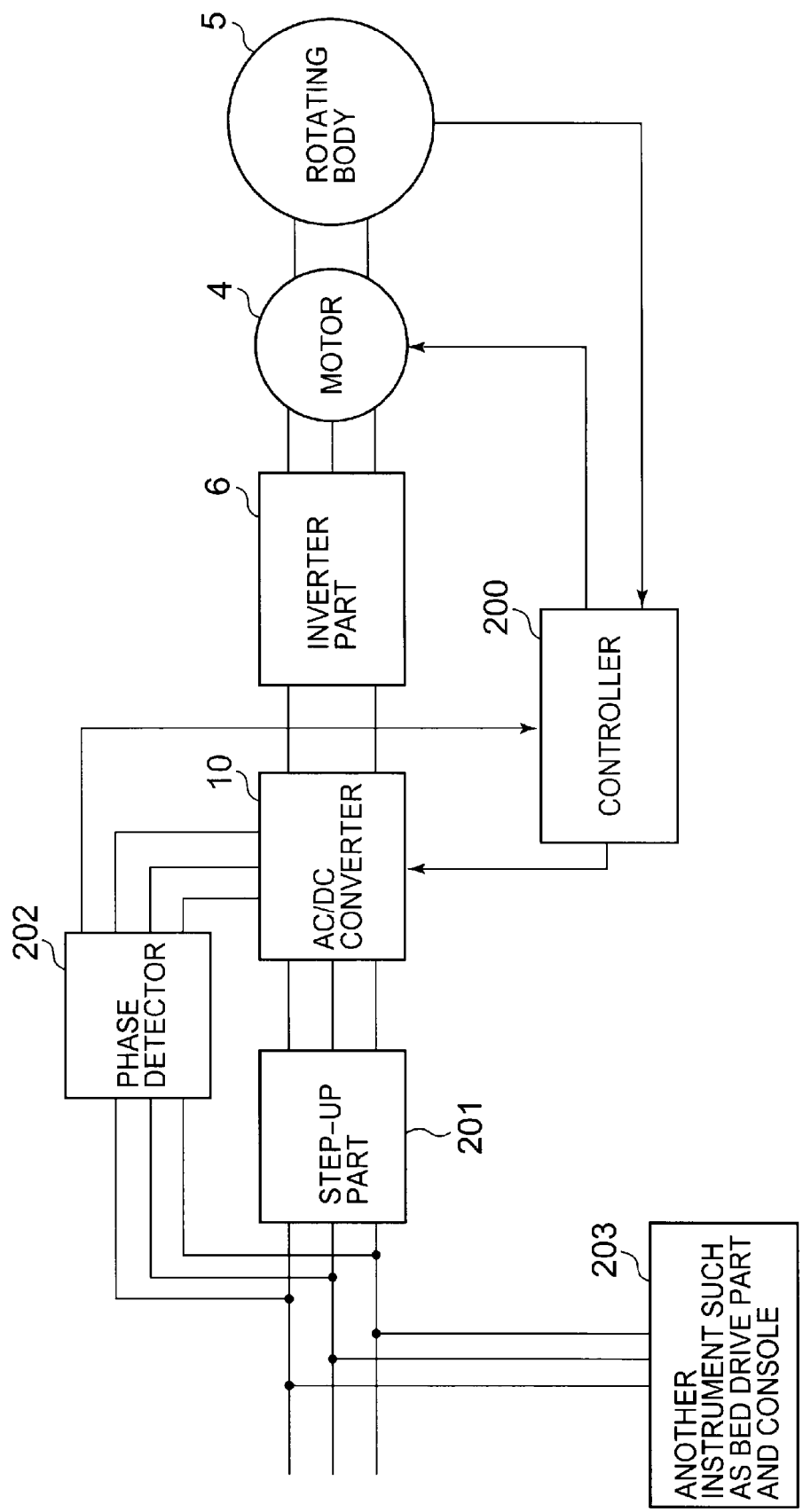
FIG. 5 is a block diagram of an X-ray CT apparatus according to a second embodiment.

Hereinafter, an X-ray CT apparatus according to the first embodiment of the present invention will be described. FIG. 5 is a block diagram representing the functions of the X-ray CT apparatus according to the present embodiment. Herein, in FIG. 5, one represented by the identical number to that in FIG. 3 shall represent one having an identical function. The operator sets the X-ray irradiation conditions, scanning conditions, image warping conditions, and the like by using a console (not shown) or the like.

The step-up part 201 comprises a transformer or the like. The step-up part 201 raises the entered voltage to the prescribed voltage.

The step-up part 201 conveys the electrical power of the raised voltage to the AC/DC converter 10.

For rotary driving of the rotating body 5, the AC/DC converter 10 converts the AC voltage conveyed from the step-up part 201 into a DC voltage. Then, the AC/DC converter 10 conveys the DC voltage to the inverter part 6. In addition, during deceleration of the rotating body 5, the AC/DC converter 10 converts the electrical power of the DC voltage conveyed from the inverter part 6 into the electrical power of an AC voltage. Furthermore, the AC/DC converter 10 conveys the AC voltage in which the adjustment of the phase, the removal of ripple, and the like have been performed by the control part 200 into another instrument 203 such as a bed drive part and a console. In other words, the AC/DC converter 10 described herein converts an AC voltage conveyed from one side into a DC voltage to output the same to the other side, and converts an DC voltage conveyed from one side into an AC voltage to output the same to the other side.

The inverter part 6 comprises IGBTs. The inverter part 6 converts the DC voltage conveyed from the AC/DC converter 10 into the electrical power of an AC voltage for driving the motor and conveys the same to the motor 4. In addition, during deceleration of the rotating body 5, the inverter part 6 conveys the regenerative electrical power generated from the motor 4 to the AC/DC converter 10.

Figure 6:
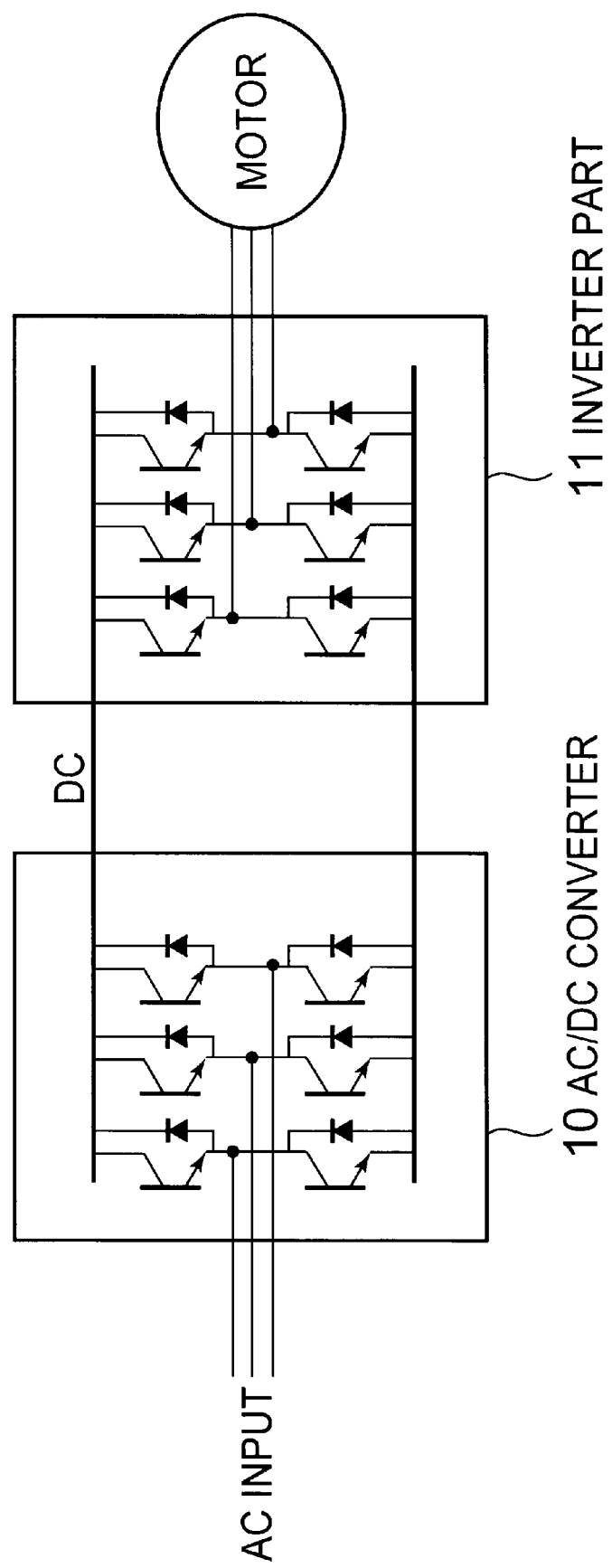
FIG. 6 is a diagram schematically representing details of an AC/DC conversion part and an inverter part in the X-ray CT apparatus according to the second embodiment.

Hereinbelow, the AC/DC converter 10 and the inverter part 6 will be described in further detail. FIG. 6 is a diagram that schematically represents details of the AC/DC converter 10 and the inverter part 6. The AC/DC converter 10 shown in FIG. 6 converts the AC voltage conveyed from the step-up part 201 into a DC voltage via a rectifying circuit part consisting of diodes. The inverter part 6 converts the DC voltage conveyed from the AC/DC converter 10 into the electrical power of an AC voltage and conveys the same to the motor by causing the switching elements such as transistors to perform a switching operation. This employs a typical motor control (such as PWM control). In addition, when the voltage of the regenerative electrical power conveyed from the motor 4 reaches a certain voltage or higher, the inverter part 6 switches the operation of the switching elements in the AC/DC converter 10 so as to supply the electrical power on the side of the DC voltage line to the line on the side of an AC voltage. Thus, the AC/DC converter 10 converts the DC voltage entered from the inverter part 6 into an AC voltage, is controlled by the control part 200 to perform switching so as to adapt to the phase of the entered waveform, and then return the AC voltage to the input line. The AC/DC converter 10 is equivalent to the "AC/DC conversion part" in the present invention.

The motor 4 rotates the rotating body 5 centered on a subject lying on a bed by using the electrical power conveyed from the inverter part 6. Furthermore, during deceleration of the rotating body 5, the motor 4 generates a regenerative electrical power and conveys the regenerative electrical power to the inverter part 6. This regenerative electrical power has the same voltage as the voltage during the rotary driving of the rotating body 5. The motor 4 and inverter part 6 is equivalent to the "drive part" in the present invention.

While the rotating body 5 is rotated, X-rays are irradiated at the subject placed on the bed from the X-ray-generator (not shown).

Furthermore, the X-ray-detector (not shown) detects the X-rays that have passed through the subject. In addition, the bed is driven by the bed drive part. When the diagnosis via the X-ray irradiation has ended, the rotating body 5 begins to decelerate.

The phase detector 202 variously detects the phase of the AC voltage to be conveyed to the step-up part 201 (hereinafter referred to as the "first phase") and the phase of the voltage conveyed from the inverter part 6 and converted into an AC voltage via the AC/DC converter 10 (hereinafter referred to as the "second phase").

Upon receipt of the entry from the console (not shown) or the like to start, the control part 200 sends an instruction to start rotation of the rotating body 5 to the inverter part 6 and the motor 4. Then, the control part 200 continually detects the rotational speed of the rotating body 5 via a rotating body detector.

Next, at a preset timing, the control part 200 sends an instruction to stop the rotating body 5 to the inverter part 6 and the motor 4. Moreover, in response to the first and second phases detected by the phase detector 202, the control part 200 controls the second phase of the outputted AC voltage by changing the operation timing of the switching elements in the AC/DC converter 10 so that each phase difference is 0. Furthermore, the control part 200 removes the ripple of the second phase that has been converted into an AC voltage via the AC/DC converter 10. The control part 200 is equivalent to the "control part" in the present invention.

The other instruments 203, including the bed drive part and the console, in FIG. 5 show the instruments driven by using an electrical power from instruments other than the motor 4 or the rotating body 5 shown in FIG. 5. Other instruments 203 are normally driven by using the voltage entered externally without change. Then, when the rotating body 5 decelerates and a recurrent voltage is generated at the motor 4, the voltage converted into an AC voltage via the AC/DC converter 10, the phase of which is adapted to the first phase via the control part 200, is conveyed to other instruments 203 along with the electrical power entered externally. In this case, the electrical power conveyed from the AC/DC converter 10 is higher than the voltage entered externally and is thus preferentially used to drive other instruments 203.

Figure 7:
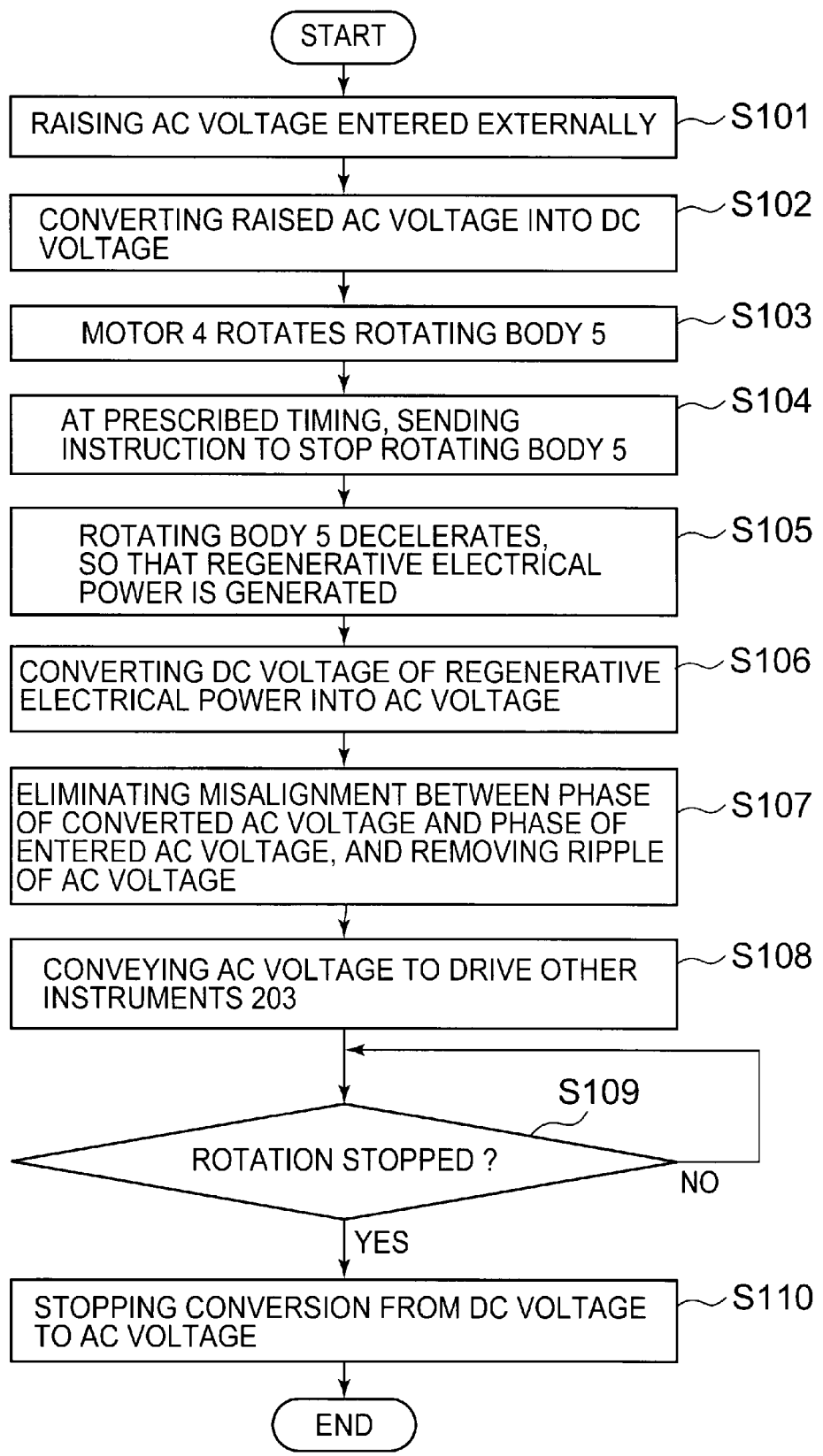
FIG. 7 is a flow chart of using regenerative electrical powers in the X-ray CT apparatus according to the second embodiment.

Next, the operations for using regenerative electrical powers in the X-ray CT apparatus according to the present embodiment will be described with reference to FIG. 7. FIG. 7 is a flow chart of using regenerative electrical powers in the X-ray CT apparatus according to the present embodiment.

Step S101: The step-up part 201 raises the AC voltage entered externally.

Step S102: The AC/DC converter 10 converts the raised AC voltage into a DC voltage.

Step S103: Upon receiving an instruction from the control part 200 to rotate the rotating body 5, the motor 4 rotates the rotating body 5 by using the DC voltage conveyed from the AC/DC converter 10 via the inverter 6.

Step S104: When the prescribed timing has been reached, such as upon the completion of imaging, the control part 200 sends an instruction to the inverter part 6 and the motor 4 to stop the rotating body 5.

Step S105: The rotating body 5 decelerates, and the motor 4 generates regenerative electrical power.

Step S106: The AC/DC converter 10 converts the DC voltage of the regenerative electrical power into an AC voltage.

Step S107: The control part 200 eliminates misalignment between the phase of the converted AC voltage and the phase of the entered AC voltage, and further removes the ripple of the AC voltage.

Step S108: The AC/DC converter 10 conveys the AC voltage in which the phase has been adjusted and the ripple is removed to other instruments 203 such as the bed drive part and the console to drive other instruments 203.

Step S109: The control part 200 determines whether rotation of the rotating body 5 has stopped. If the rotation has stopped, it proceeds to Step S110.

Step S110: The control part 200 controls the AC/DC converter 10 to stop the conversion from a DC voltage to an AC voltage.

As described above, the X-ray CT apparatus according to the present embodiment can use the regenerative electrical power generated due to deceleration of the rotating body to drive other instruments. This eliminates the need for an accumulation part for charging the regenerative electrical power, so it is possible to make the size of the X-ray CT apparatus more compact. In addition, because the regenerative electrical power can be used for another bed drive part, console, or the like, it becomes possible to efficiently use the generated electrical power and to contribute more fully to energy saving.

Embodiment 3

Figure 1:
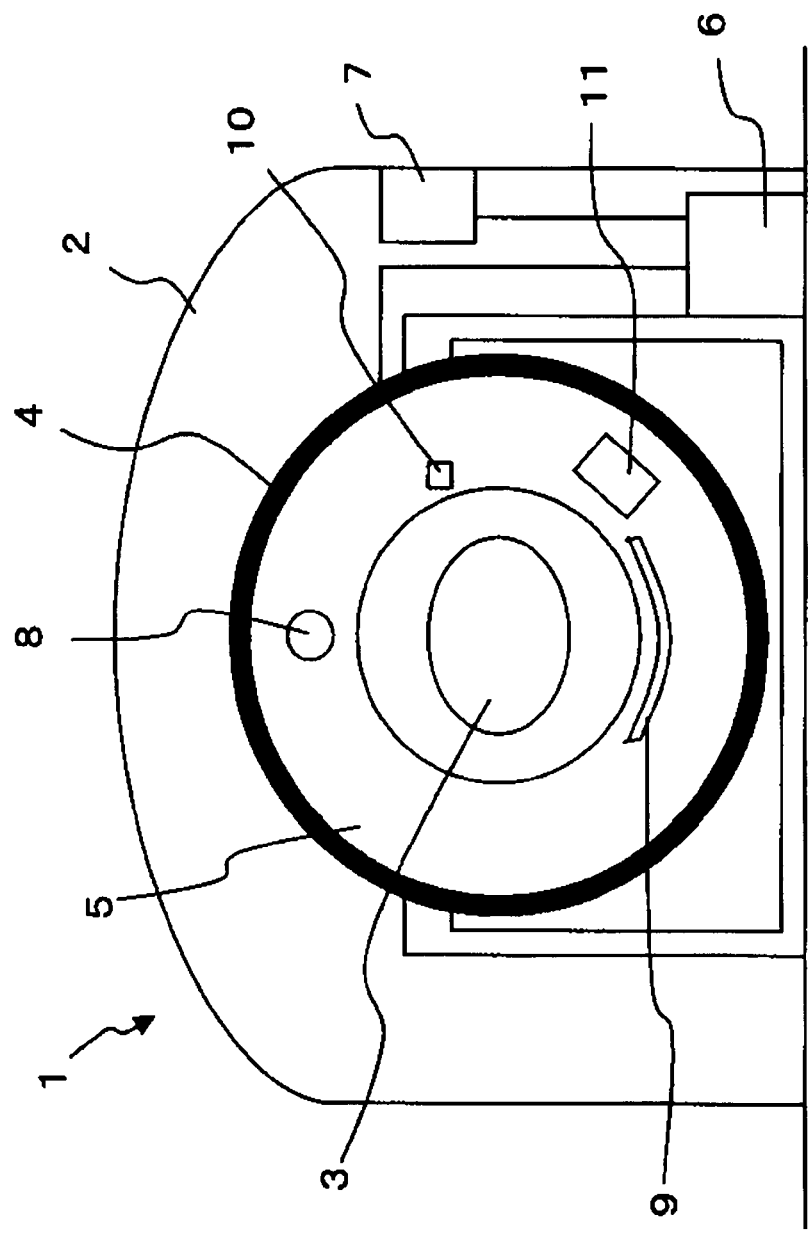
FIG. 1 is a front perspective diagram representing an outline of the constitution of a conventional X-ray CT apparatus.
Figure 2:
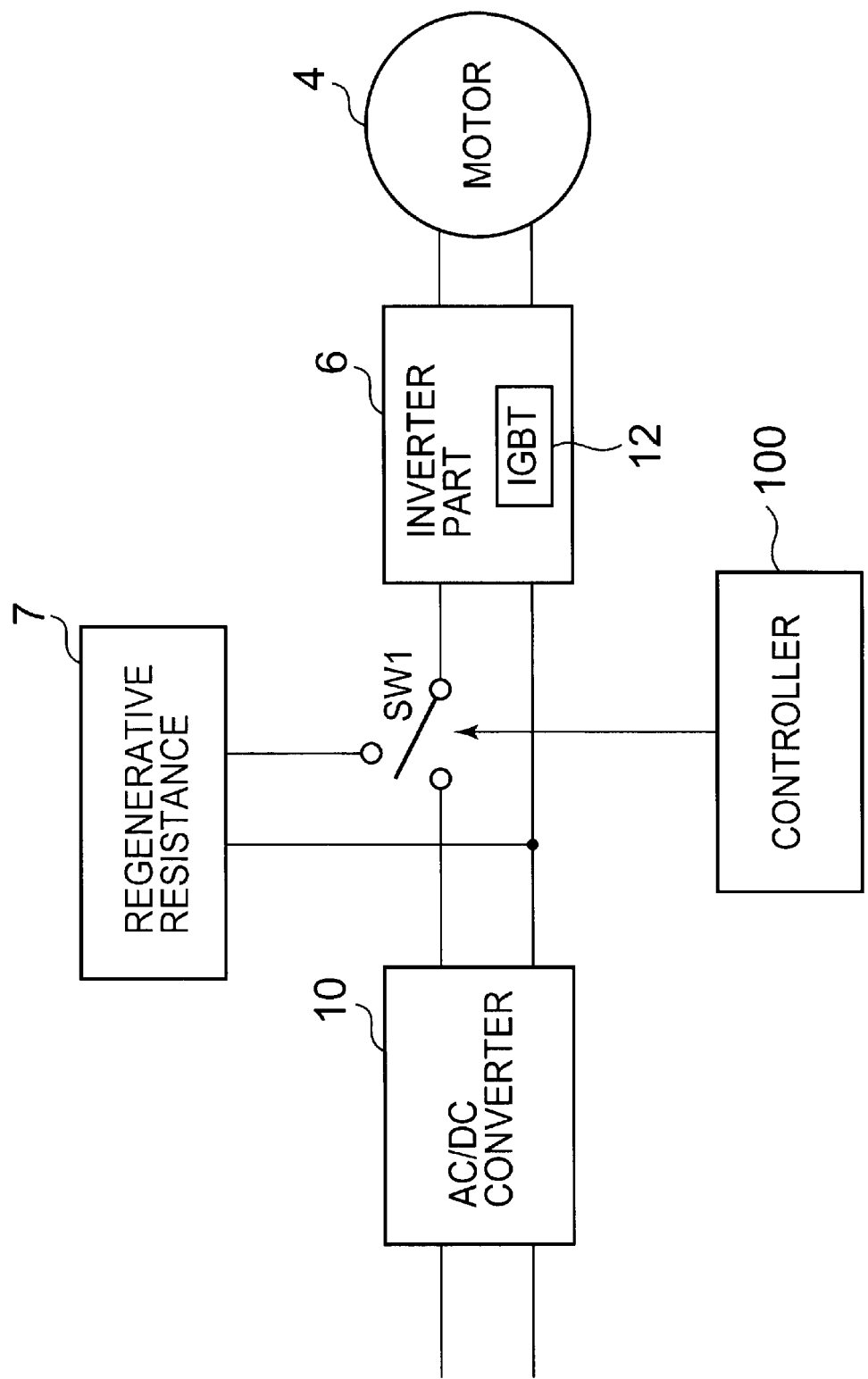
FIG. 2 is a block diagram of a conventional X-ray CT apparatus.

The X-ray CT apparatus according to the present embodiment differs from the first embodiment in that it is configured to supply the electricity accumulated in the accumulation part to another structural unit such as an image-processing apparatus, a bed drive part, or a console. Then, hereinafter, the constitution and operations for supplying the electrical power accumulated in the accumulation part to another structural unit will mainly be described. The block diagram of the X-ray CT apparatus according to the present embodiment is a functional block of the X-ray CT apparatus according to the first embodiment shown in FIG. 1 to which a functional block represented by dotted lines has been added.

The Electric Double Layer Capacitor 101 is connected to the step-up chopper 103 and the voltage-transforming part 301 as destinations of the power supply.

Then, the electrical power accumulated in the Electric Double Layer Capacitor 101 is supplied to the voltage-transforming part 301.

Power is supplied to the voltage-transforming part 301 regardless of whether the electrical power accumulated in the Electric Double Layer Capacitor 101 is controlled by the control part 100 to be supplied to the step-up chopper 103.

The voltage-transforming part 301 lowers (or raises) the voltage of the electrical power supplied from the Electric Double Layer Capacitor 101 and transforms the same to a voltage that may be used in another structural unit 302. Herein, when sufficient electricity is accumulated in the Electric Double Layer Capacitor 101, the voltage-transforming part 301 transforms the electrical power to a voltage higher than the voltage of the electrical power supplied externally and supplies the electrical power to another structural unit 302.

The voltage-transforming part 301 supplies the transformed electrical power to another structural unit 302.

The other structural unit 302 is also externally supplied with electrical power. Then, the other structural unit 302 performs image processing, driving of a bed, or the like by using either a voltage higher than the voltage supplied from the voltage-transforming part 301 or the voltage supplied externally. Herein, when a sufficient amount of electricity is accumulated in the Electric Double Layer Capacitor 101, the electrical power with a voltage higher than the electrical power supplied externally is supplied from the voltage-transforming part 301, so the electrical power supplied from the Electric Double Layer Capacitor 101 will be used.

As described above, the X-ray CT apparatus according to the present embodiment is configured so that the electrical power of the Electric Double Layer Capacitor 101 is always supplied to the other structural unit 302. This makes it possible to reduce the saturation of accumulated electrical power in the Electric Double Layer Capacitor 101. Thus, it becomes possible to easily set the capacity of the Electric Double Layer Capacitor 101. In addition, because the accumulated electrical power is used not only for driving the rotating body 5 but also for another structural unit 302, it is possible to further save energy.

Moreover, in the present embodiment, a voltage-transforming part 301 that is directly supplied with electrical power from the Electric Double Layer Capacitor 101 is provided in addition to the step-up chopper 103. However, another constitution is also possible: for example, it may be configured to lower the voltage of the electrical power that has been raised via the step-up chopper 103 to supply the same to another structural unit 302.

What is claimed is:

1. An X-ray CT apparatus comprising:
    an X-ray-generator configured to irradiate X-rays at a subject;
    an X-ray-detector configured to detect the X-rays that have permeated said subject;
    a rotating body on which said X-ray-generator and said X-ray-detector are installed to be rotated around said subject;
    a drive part configured to rotate said rotating body;
    a power source configured to supply electrical power to said drive part;
    a step-down part configured to lower the voltage of regenerative electrical power generated at said drive part during deceleration of said rotating body;
    an accumulation part configured to charge said lowered electrical power; and
    a step-up part configured to raise the voltage of electrical power from said accumulation part and configured to supply electrical power to said drive part.

2. The X-ray CT apparatus according claim 1, further comprising:
    a switch control part: configured to supply electrical power from said power source to said drive part when said accumulation part is at a predetermined voltage or less while driving said rotating body; configured to supply electrical power to said drive part from said accumulation part when said accumulation part is at a predetermined voltage or more while driving said rotating part; and configured to switch so as to supply the electrical power generated at said drive part to said accumulation part when decelerating said rotating body.

3. The X-ray CT apparatus according the claim 1, further comprising:
a voltage-transforming part configured to raise or lower voltage from said accumulation part and configured to supply electrical power to another structural unit including any one of an image-processing apparatus, a bed drive part, or a console, or a combination thereof.

4. The X-ray CT apparatus according the claim 1, further comprising:
a controller configured to detect rotational speed of said rotating body and, after rotation stops, configured to connect the step-up part to a power supply pathway of said drive part.

5. An X-ray CT apparatus, comprising:
a bed on which to place a subject;
a bed drive part configured to drive said bed;
an X-ray-generator configured to irradiate X-rays at a subject;
an X-ray-detector configured to detect the X-rays that have permeated said subject;
a rotating body on which said X-ray-generator and said X-ray-detector are installed for rotating around said subject;
a drive part configured to rotate said rotating body;
a step-up part configured to raise an alternating-current voltage that is entered externally;
an AC/DC conversion part configured to convert said raised alternating-current voltage into direct-current voltage to convey the same to said drive part during rotating said rotating body, and, when said rotating body decelerates, configured to convert regenerative electrical power generated at said drive part during deceleration of said rotating body into an alternating-current voltage to supply electrical power to at least one of said bed drive part or an image-processing part; and
a controller configured to match the phase of the voltage of the regenerative electrical power that has been conveyed to said AC/DC conversion part to a phase of said alternating-current voltage that is entered externally.

6. An X-ray CT apparatus, comprising:
a bed on which to place a subject;
a bed drive part configured to drive said bed;
an X-ray-generator configured to irradiate X-rays at a subject;
an X-ray-detector configured to detect the X-rays that have permeated said subject;
a rotating body on which said X-ray-generator and said X-ray-detector are installed for rotating around said subject;
a drive part configured to rotate said rotating body;
a step-up part configured to raise an alternating-current voltage that is entered externally;
an AC/DC conversion part configured to convert said raised alternating-current voltage into direct-current voltage to convey the same to said drive part during rotating said rotating body, and, when said rotating body decelerates, configured to convert regenerative electrical power generated at said drive part during deceleration of said rotating body into an alternating-current voltage to supply electrical power to at least one of said bed drive part or an image-processing part; and
a controller configured to detect a number of rotations of said rotating body and, after rotation of said rotating body stops, to disconnect the power supply pathway from the AC/DC conversion part to at least said bed drive part and image-processing part.

7. A method of controlling an X-ray CT apparatus comprising:
supplying electrical power from a power source;
rotating a rotating body around a subject via a drive part by using said supplied electrical power;
irradiating X-rays at said subject from an X-ray-generator installed on said rotating body;
detecting the X-rays that have permeated said subject via an X-ray-detector installed on said rotating body;
lowering the voltage of regenerative electrical power generated at said drive part during deceleration of said rotating body;
charging said lowered electrical power into said an accumulation part; and
raising the voltage of the electrical power from said accumulation part by a step-up part and supplying electrical power to said drive part in order to drive said rotating body.

8. The method of controlling an X-ray CT apparatus according to claim 7, further comprising:
switching a power supply pathway to a pathway for charging the accumulation part during deceleration of said rotating body prior to said accumulation, and
switching the power supply pathway, prior to rotating said rotating body after said accumulation, to the power supply pathway from said accumulation part at a time of next rotation after said rotation body has stopped.

9. The method of controlling an X-ray CT apparatus according to claim 7, further comprising:
raising or lowering the voltage from said accumulation part and supplying electrical power to another structural unit, including any one of an image-processing apparatus, a bed drive part, or a console, or a combination thereof, after said accumulation.

10. The method of controlling an X-ray CT apparatus according to claim 7, further comprising:
detecting the rotational speed of said rotating body and, after rotation stops, to connect the step-up part to a power supply line of said drive part.

11. The method of controlling an X-ray CT apparatus, comprising:
raising an alternating-current voltage that is entered externally;
converting said raised alternating-current voltage into direct-current voltage to convey the same to a drive part configured to rotate a rotating body;
rotating said rotating body around a subject via said drive part;
irradiating X-rays at said subject from an X-ray-generator installed on said rotating body;
detecting the X-rays that have permeated said subject via an X-ray-detector installed on said rotating body;
converting regenerative electrical power generated at said drive part during deceleration of said rotating body into an alternating-current voltage;
supplying said alternating-current voltage from said drive part to at least one of a bed drive part for driving a bed or an image-processing part; and
matching the phase of the voltage of said regenerative electrical power that has been converted to said alternating-current voltage to the phase of the alternating-current voltage that is entered externally.

12. A method of controlling an X-ray CT apparatus, comprising:

a bed on which to place a subject;

a bed drive part configured to drive said bed;

an X-ray-generator configured to irradiate X-rays at a subject;

an X-ray-detector configured to detect the X-rays that have permeated said subject;

a rotating body on which said X-ray-generator and said X-ray-detector are installed for rotating around said subject;

a drive part configured to rotate said rotating body;

a step-up part configured to raise an alternating-current voltage that is entered externally;

an AC/DC conversion part configured to convert said raised alternating-current voltage into direct-current voltage to convey the same to said drive part during rotating said rotating body, and, when said rotating body decelerates, configured to convert regenerative electrical power generated at said drive part during deceleration of said rotating body into an alternating-current voltage to supply electrical power to at least one of said bed drive part or an image-processing part; and detecting a number of rotations of said rotating body and, after rotation of said rotating body stops, disconnecting the power supply from the AC/DC conversion part to at least said bed drive part and image-processing part.

* * * * *